(12) United States Patent
Fujimoto et al.

(10) Patent No.: US 7,810,200 B2
(45) Date of Patent: Oct. 12, 2010

(54) ELECTRIC TOOTHBRUSH

(75) Inventors: Norioki Fujimoto, Otsu (JP); Toru Kamimura, Maibara (JP); Junji Matsue, Gunma (JP)

(73) Assignee: Sanyo Electric Co., Ltd., Moriguchi-shi (JP)

( * ) Notice: Subject to any disclaimer, the term of this patent is extended or adjusted under 35 U.S.C. 154(b) by 1365 days.

(21) Appl. No.: 11/274,146

(22) Filed: Nov. 16, 2005

(65) Prior Publication Data

US 2006/0101598 A1    May 18, 2006

(30) Foreign Application Priority Data

Nov. 17, 2004   (JP) .............................. 2004-332960

(51) Int. Cl.
*A61C 17/34*   (2006.01)
(52) U.S. Cl. ........................................ 15/22.2; 74/22 A
(58) Field of Classification Search ................. 15/21.1, 15/22.1, 22.2; 74/22 A, 25
See application file for complete search history.

(56) References Cited

U.S. PATENT DOCUMENTS 5,253,382 A * 10/1993 Beny .......................... 15/22.1

FOREIGN PATENT DOCUMENTS

| GB | 2398487 | * | 8/2004 |
| JP | 9-24057 | | 1/1997 |
| JP | 9-177923 | | 7/1997 |
| WO | WO 02/067806 | * | 9/2002 |

* cited by examiner

*Primary Examiner*—Laura C Guidotti
(74) *Attorney, Agent, or Firm*—Westerman, Hattori, Daniels & Adrian, LLP (57) ABSTRACT

An electric toothbrush wherein the number of revolution of a motor shaft is in match with the frequency of reciprocating motion of the brush. A motor (2) housed in a tubular case (1) is coupled to a reciprocating shaft (5) slidably extending through the forward end of the case by a scotch yoke mechanism (40) for converting one turn of rotation of the motor shaft (21) into one stroke of reciprocating pivotal movement of a pivotal body (4), and by motion conversion means (3) for converting one stroke of reciprocating movement of the pivotal body (4) into one stroke of linear reciprocating motion of the reciprocating shaft (5).

6 Claims, 9 Drawing Sheets

PRIOR ART

FIG. 17

PRIOR ART

ELECTRIC TOOTHBRUSH

FIELD OF THE INVENTION

The present invention relates to electric toothbrushes for brushing teeth by the Bass method using a motor as a power source.

BACKGROUND OF THE INVENTION

Figure 16:
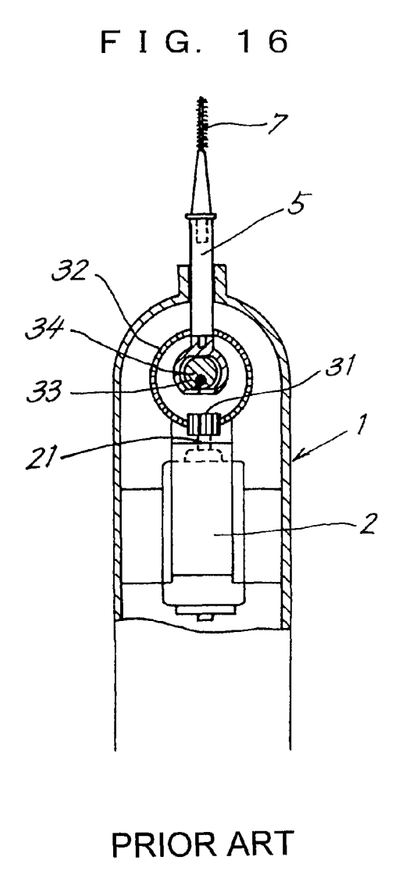
FIG. 16 is a fragmentary view in section of a conventional electric toothbrush.
Figure 17:
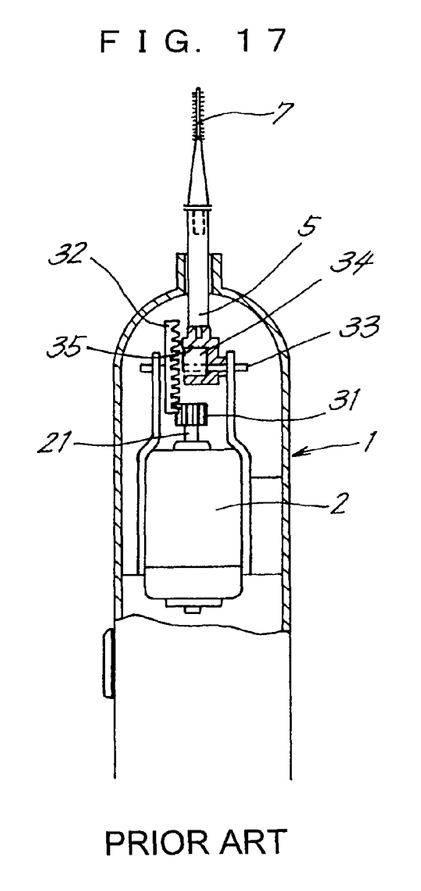
FIG. 17 is a fragmentary view in section of the electric toothbrush of FIG. 16 as it is seen from a lateral direction.

With reference to FIGS. 16 and 17 showing an electric toothbrush for practicing the Bath method (reciprocating motion), the toothbrush comprises a tubular case 1 serving also as a handle, a motor 2 housed in the case 1 and having a motor shaft 21 extending along the axis of the case 1, and a reciprocating shaft 5 having a brush member 7 and reciprocatingly drivable by the rotation of the motor shaft 21 as converted into a linear movement approximately along the axis of the case 1 by motion conversion means.

For example according to JP-A No. 9-24057 and JP-A No. 9-177923, a pinion gear 31 mounted on the motor shaft 21 is in mesh with a crown gear 32 perpendicular to the axis of the gear 31. A rotating shaft 33 for the crown gear 32 has mounted thereon an eccentric rotating body 34, which is rotatably fitted in a cavity 35 in a base end of the reciprocating shaft 5 reciprocatingly movable approximately along the axis of the case 1 to provide a scotch yoke mechanism, whereby the rotation of the motor shaft 21 is converted into linear motion.

With electric toothbrushes of the Bass type, the frequency of reciprocating motion of the brush member is considered important.

With the conventional motion conversion means, the rotation of the motor shaft 21 is delivered to the scotch yoke mechanism (cross slider mechanism) upon a reduction at the gear ratio between the pinion gear 31 and the crown gear 31, so that the frequency of the reciprocating motion of the brush member 7 invariably becomes smaller than the number of revolutions of the motor shaft 21.

Because of the construction wherein the scotch yoke mechanism is provided coaxially with the rotating shaft 33 of the crown gear 32, the crown gear is positioned out of alignment with the axis of the tubular case 1, such that as the crown gear 32 is positioned a larger distance away from the case axis, the crown gear 32 needs to have a smaller outside diameter. The larger the crown gear 32 in outside diameter, the more advantageously the gear 31 meshes with the pinion gear 31, whereas this invariably reduces the number of teeth because of the limitation imposed by the outside diameter. Further to give a satisfactory outside diameter to the pinion gear 31 to be in mesh with the crown gear 32, the crown gear 32 needs to be positioned a greater distance away from the axis of the tubular case 1. Consequently, the pinion gear 31 and the crown gear 32 become smaller in the number of teeth, and the meshing engagement between the gears 31, 32 involves a greater backlash, producing vibration and noise and impairing the smoothness of reciprocating motion.

In the case where the scotch yoke mechanism is shaped to have the smallest possible thickness in order to avoid the above problems, the mechanism becomes liable to brittle fracture due to a reduction in the strength of the material. Furthermore a diminished tooth profile module will result in view of the need to assure the pinion gear 31 of strength. This increases the gear ratio between the pinion gear 31 and the crown gear 32 to reduce the frequency of the reciprocating motion.

Further because the tubular case 1 serves also as a handle, the thickness of the case 1 is limited from the viewpoint of ease of gripping and design, consequently limiting the gear ratio between the pinion gear 31 and the crown gear 32 to a certain range. For this reason, the conventional construction involves diminished freedom of design in giving an increased frequency to the brushing motion, consequently posing an obstacle in improving the performance with respect to vibration and noise.

SUMMARY OF THE INVENTION

An object of the present invention is to provide an electric toothbrush which is made free of the above problems by devising novel means for converting the rotation of the motor shaft into reciprocating motion.

The present invention provides a first electric toothbrush which comprises a motor housed in a case, motion conversion means for converting the rotation of a motor shaft of the motor into reciprocating motion approximately along an axis of the motor shaft, and a brush member movable with the reciprocating motion, the motor shaft being provided with an eccentric rotating body rotatable with the rotation of the motor shaft, the motion conversion means having a pivotal body supported by a rod and pivotally movable in a plane orthogonal to the motor shaft, the pivotal body having a portion slidably engaged with the eccentric rotating body and being pivotally movable by the rotation of the eccentric rotating body, the motion conversion means further having a reciprocating shaft provided with the brush member and connected to another portion of the pivotal body to reciprocatingly move with the pivotal movement of the pivotal body and to cause the brush member to perform reciprocating motion.

With the first electric toothbrush of the invention, one turn of rotation of the motor shaft reciprocatingly pivotally moves the pivotal body by one stroke, and one stroke of reciprocating pivotal movement of the pivotal body causes the reciprocating shaft to reciprocatingly move approximately along the axis of the tubular case one stroke. Thus, one turn of rotation of the motor shaft causes the brush member on the reciprocating shaft to perform one forward and backward stroke.

Unlike the conventional electric toothbrush, therefore, it is unlikely that the frequency of reciprocating motion of the brush member will be smaller than the number of revolutions of the motor shaft.

The present invention provides a second electric toothbrush which comprises a tubular case serving also as a handle, a motor housed in the tubular case so as to position a motor shaft approximately along an axis of the tubular case, a reciprocating shaft coupled to the motor shaft by motion conversion means for converting the rotation of the motor shaft into reciprocating motion approximately along the axis of the tubular case, and a brush member attached to the reciprocating shaft, the motion conversion means having a pivotal body pivotally movable about a support rod extending in a direction orthogonal to the motor shaft, and an eccentric rotating body provided on the motor shaft and engaged with a portion of the pivotal body positioned toward the motor shaft for pivotally moving the pivotal body so as to provide a scotch yoke mechanism, the reciprocating shaft being pivotally connected to the pivotal body to cause the brush member to perform reciprocating motion.

In addition to the advantage of the first electric toothbrush, the second electric toothbrush of the invention can be reduced in size because the case is tubular and serves also as a handle.

With the electric toothbrush described above, the pivotal body may have a rectangular frame for the eccentric rotating body to slidably rotatably fit in and may be pivotally movably supported by the support rod, and the reciprocating shaft being connected by a connecting member to a pivot positioned in the vicinity of the support rod and away from the axis of the tubular case toward a direction orthogonal to the axis of the tubular case.

With the electric toothbrush described above, the motor shaft and the center of pivotal movement of the pivotal body can be made to match with the axis of the tubular case. Since the toothbrush has neither of the pinion gear and the crown gear conventionally used, the tubular case can be given the smallest possible size. This means that the tubular case can be designed generally free of limitations and can be so designed that the case is easy to grip. The toothbrush of the invention is further free of the problem attributable to the backlash to be involved in the meshing engagement of the pinion gear and the crown gear of the prior art.

With the electric toothbrush described above, the pivotal body may have a flexible support arm extending toward the brush member from each of opposite ends thereof in the directions of pivotal movement thereof, the support arm having an outer end held by the tubular case.

With the electric toothbrush described above, the pivotal body is supported pivotally movably at three points, i.e., by the support rod, and two support arms. This stabilizes the pivotal movement of the pivotal body to result in a stabilized reciprocating brushing movement. Moreover, the construction described eliminates the noise and minute faulty irregularities involved the movement of components which are attributable to the backlashes of the frame and eccentric rotating body relative to each other to ensure facilitated assembling of the components.

With the electric toothbrush described above, the support arm can be in the form of a thin plate made from a synthetic resin integrally with the pivotal body and having a widthwise direction orthogonal to the direction of pivotal movement of the pivotal body, the support arm being made readily elastically deformable within the plane of pivotal movement of the pivotal body and difficult to elastically deform in a direction orthogonal to the direction of pivotal movement of the pivotal body.

With the electric toothbrush described above, the pivotal body and the support arms are made from a synthetic resin integrally, so that this construction results in no increase in the number of components, obviates the need to attach the support arms to the pivotal body manually and therefore suppresses a rise in cost. Furthermore, the support arms are readily elastically deformable within the plane of pivotal movement of the pivotal body but are difficult to elastically deform in a direction orthogonal to the direction of pivotal movement of the pivotal body. The pivotal body is therefore movable free of any trouble, with the support arms prevented from wobbling in a direction orthogonal to the direction of pivotal movement of the body. Thus, the pivotal body is pivotally movable with enhanced stability.

With the electric toothbrush described above, the reciprocating shaft may extend through and be supported by a flexible bearing disposed at a forward end of the tubular case.

When the reciprocating shaft is thus made to slidably extend through and supported by the flexible bearing provided at the forward end of the tubular case, the reciprocating shaft is allowed to reciprocatingly move axially thereof and also to somewhat deflect from the center of the bearing. Accordingly, the shaft can be supported free of trouble even if made reciprocatingly movable with some deflective movement With the second electric toothbrush of the invention, the pivotal body may be generally U-shaped and may comprise a connecting portion, and a rectangular frame and a bracket which are joined respectively to opposite ends of the connecting portion and opposed to each other, the eccentric rotating body being slidably rotatably fitted in the frame, the reciprocating shaft being pivotally connected to the pivotal body by a pivot supported on the bracket, the support rod being positioned in the vicinity of a bent portion of the pivotal body on the pivot side thereof and positioned in parallel to the pivot, the reciprocating shaft being pivotally movably supported by a bearing at a forward end of the tubular case.

With the electric toothbrush described above, one turn of rotation of the motor shaft causes the scotch yoke mechanism to reciprocatingly pivotally move the pivotal body about the support rod with one stroke, and one stroke of reciprocating pivotal movement of the pivotal body causes the brush member to perform a stroke of reciprocating motion through the connecting member and the reciprocating shaft. Thus, one turn of rotation of the motor shaft causes the brush member to perform one forward and backward stroke. Accordingly, it is unlikely that the frequency of reciprocating motion of the brush member will become smaller than the number of revolutions of the motor shaft.

DESCRIPTION OF THE PREFERRED EMBODIMENTS

With reference to FIGS. 1 to 6, the present invention provides an electric toothbrush, which comprises a tubular case 1 serving also as a handle, a reciprocating shaft 5 extending outward from one end of the case 1, and a brush member 7 replaceably attached to the reciprocating shaft 5.

The tubular case 1 comprises a main case member 11 and a closure case member 12 which have approximately the same size and can be separated from each other at an angle slightly inclined with respect to the axis of the case. The tubular case has a bottom 13 which is provided on the main case member 11. The reciprocating shaft 5 is positioned approximately on the axis of the tubular case 1.

Figure 1:
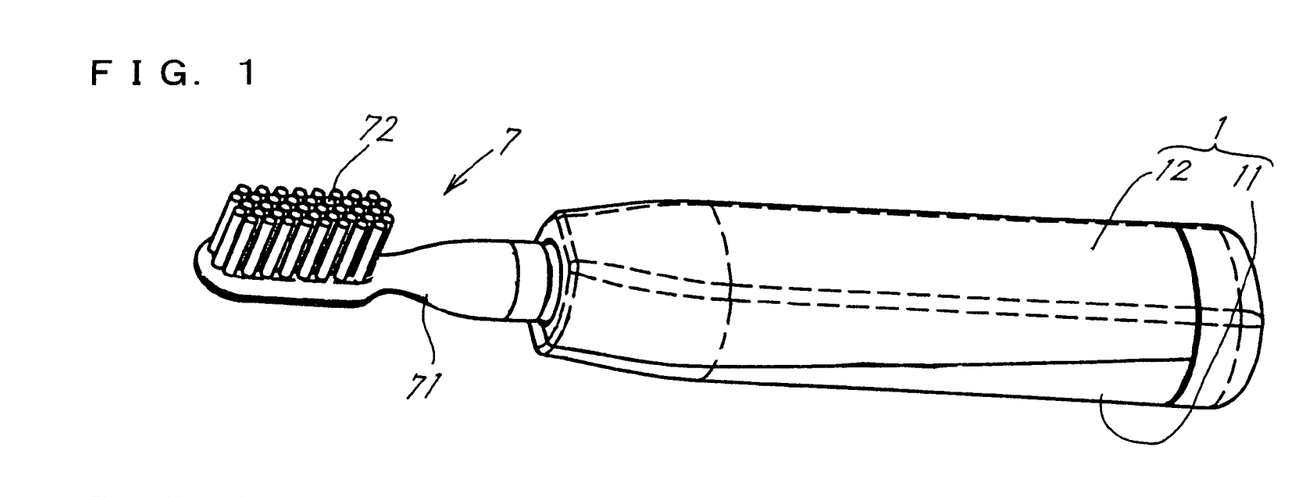
FIG. 1 is a perspective view of an electric toothbrush embodying the invention.
Figure 2:
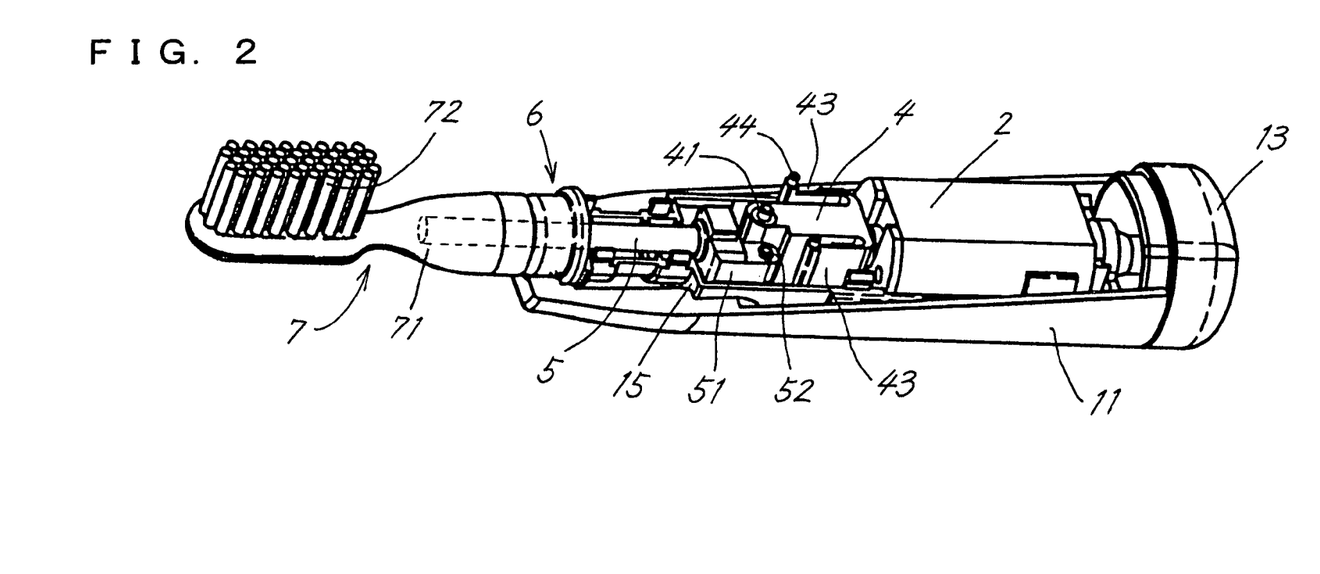
FIG. 2 is a perspective view of the electric toothbrush with a closure case of FIG. 1 omitted.
Figure 3:
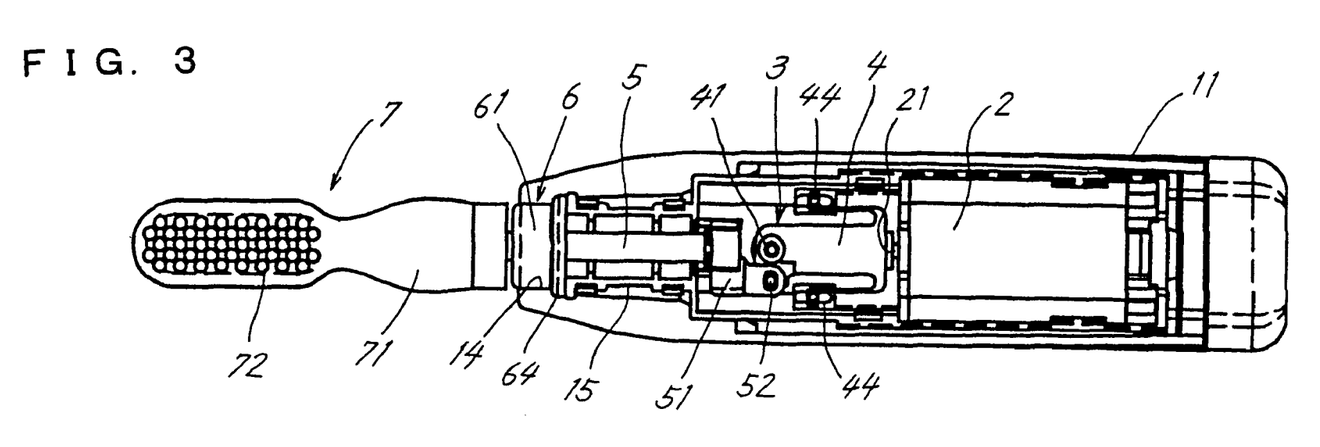
FIG. 3 is a front view of FIG. 2.
Figure 4:
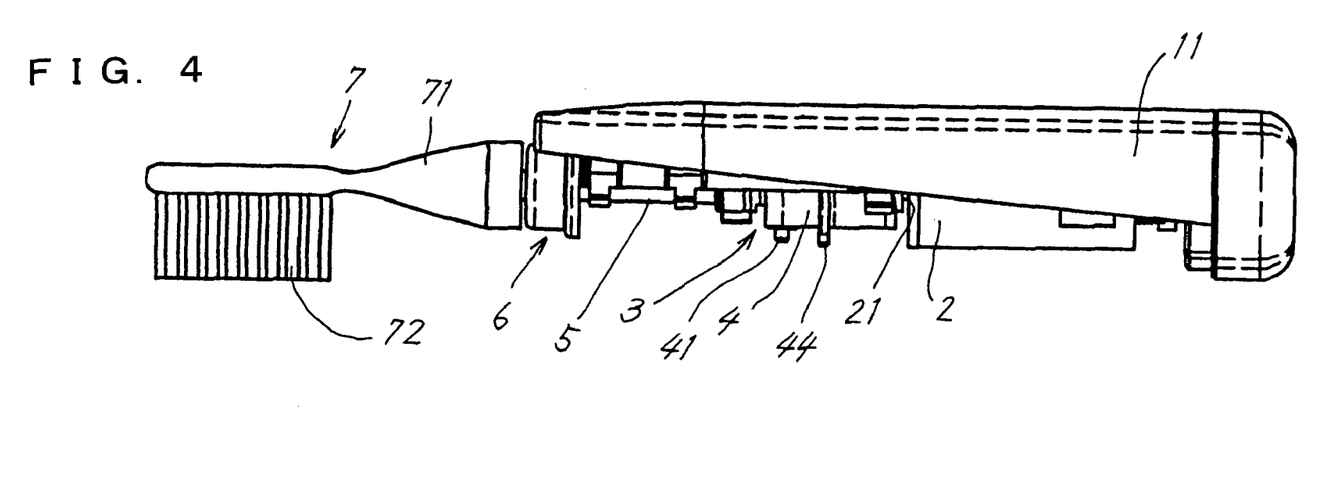
FIG. 4 is a plan view of FIG. 2.
Figure 5:
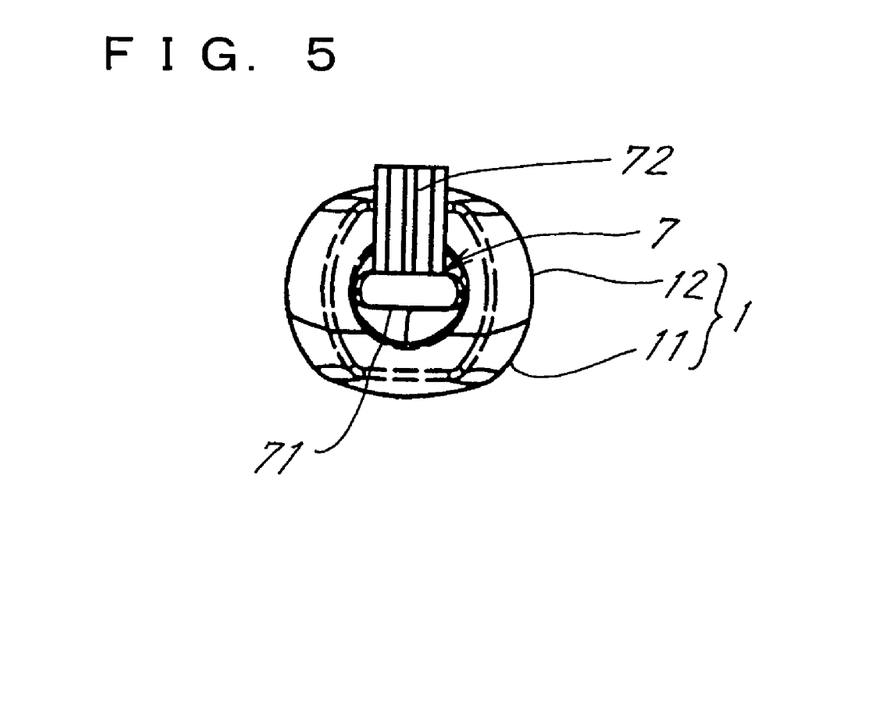
FIG. 5 is a left side elevation of FIG. 1.
Figure 6:
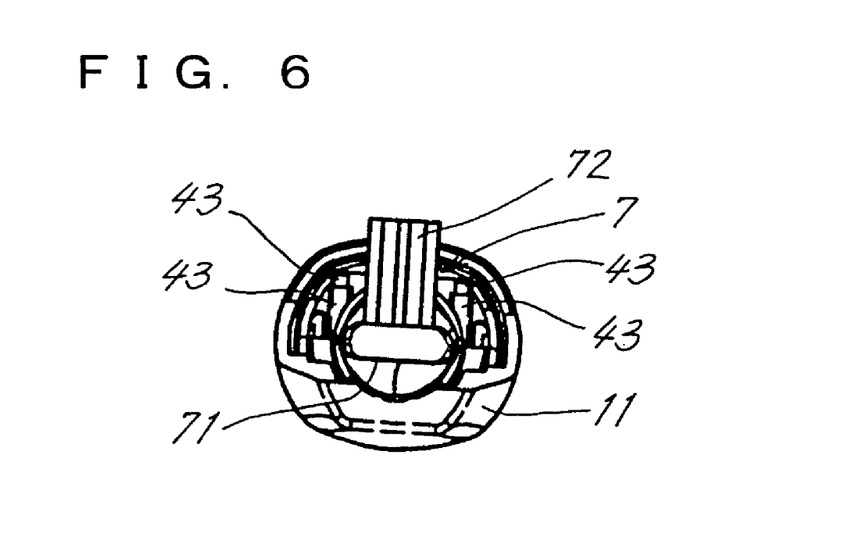
FIG. 6 is a left side elevation of FIG. 2.

To ensure watertightness, the closure case member 12 is liquid-tightly fitted to the main case member 11 and is not intended to be opened.

In the following description, the term the "front side" refers to the closure case member side, and the term the "rear side" to the main case member side.

A motor 2 is disposed in the tubular case 1 toward the bottom 13 thereof. The motor 2 has a motor shaft 21 extending toward the reciprocating shaft 5 in alignment with the axis of the tubular case 1.

The motor shaft 21 is coupled to the reciprocating shaft 5 by motion conversion means 3 for converting the rotation of the motor shaft 21 into reciprocating motion of the reciprocating shaft 5.

Also enclosed in the tubular case 1 are rechargeable battery and a motor drive circuit, which are not shown in the drawings.

With reference to FIGS. 7 to 11, the motion conversion means 3 comprises a pivotal body 4 pivotably provided between the motor shaft 21 and the reciprocating shaft 5, a scotch yoke mechanism (cross slider mechanism) for converting the rotation of the motor shaft 21 into a pivotal movement of the pivotal body 4, and a connecting member 51 for connecting the pivotal body 4 to the reciprocating shaft 5.

The pivotal body 4 is a rectangular parallelepipedal block made from a synthetic resin and elongated axially of the tubular case 1, and is disposed on the axis of the tubular case 1 between the motor shaft 21 and the reciprocating shaft 5. The pivotal body 4 is provided at one end thereof closer to the reciprocating shaft 5 with short support rods 41, 41 projecting from opposite positions on the front and rear sides of the body 4 and fitting in respective bearing holes (not shown) formed in the inner surfaces of the main case member 11 and the closure case member 12, whereby the pivotal body 4 is supported so as to be pivotally movable about the support rods 41.

The support rods 41, 41 are positioned within a plane containing the axis of the tubular case 1.

Figure 8:
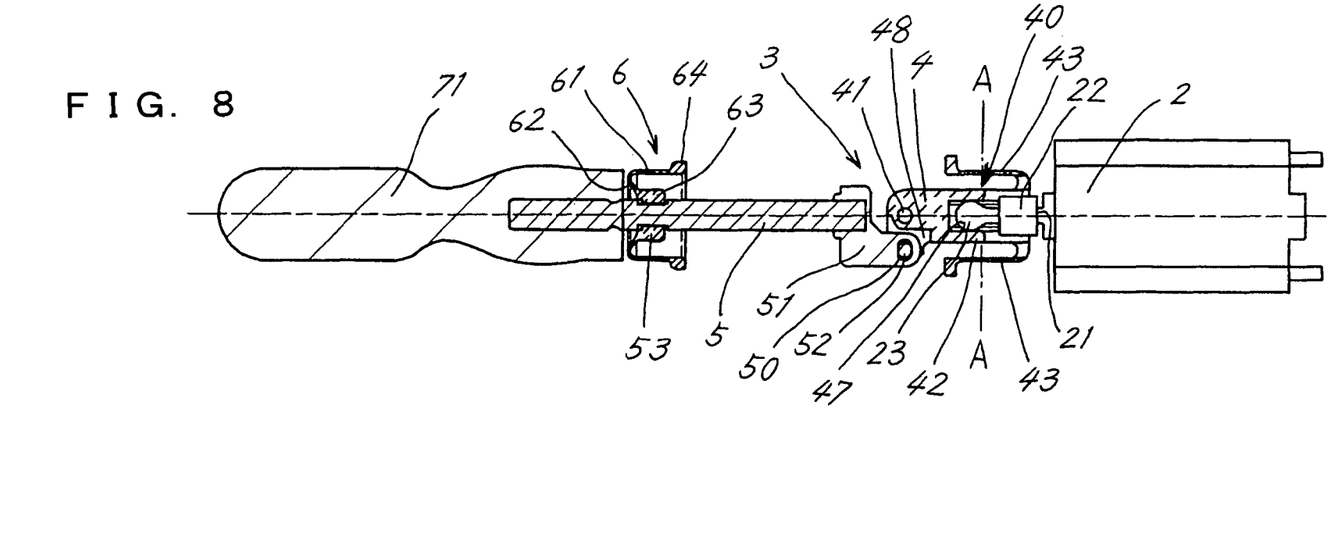
FIG. 8 is a diagram showing the motion conversion means partly in section.

As shown in FIG. 8, the pivotal body 4 has a frame 42 positioned close to the motor shaft 21 and having slidably fittingly engaged therein an eccentric rotating body 23 which is provided on the motor shaft 21, whereby the scotch yoke mechanism 40 is constructed.

The eccentric rotating body 23 rotatably projects from a boss 22 mounted on the motor shaft 21 at an eccentric position thereon and having a spherical face slidable in contact with the frame 42.

Figure 9:
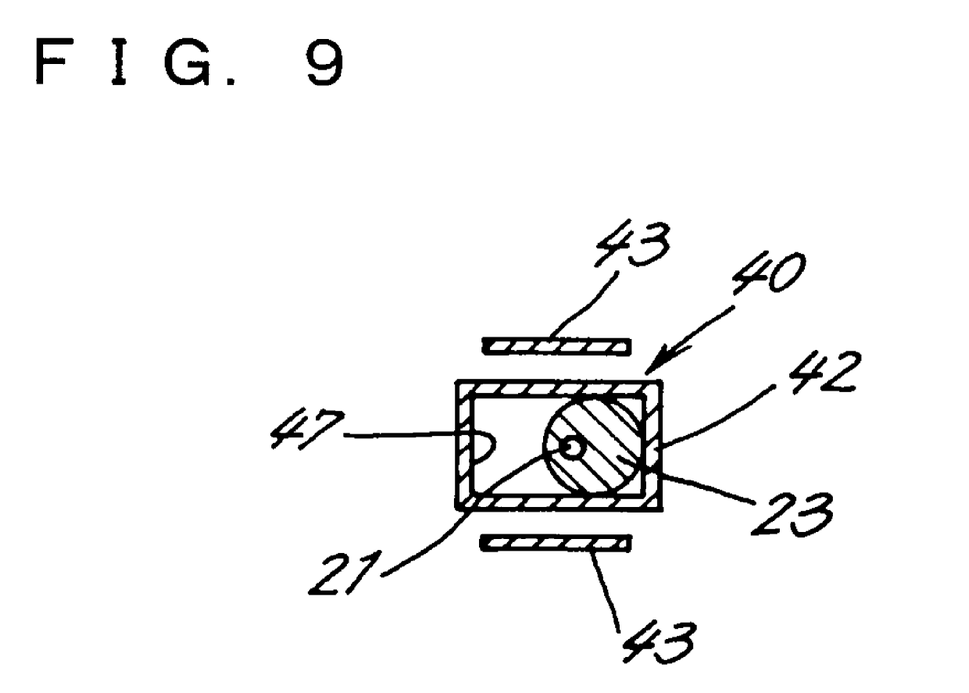
FIG. 9 is a view in section taken along the line A-A in FIG. 8.

The frame 42 is provided by forming a rectangular bore 47 in the pivotal body 4 at the end thereof closer to the motor shaft 21. As shown in FIG. 9, the rectangular bore 47 is elongated in the front-rear direction of the tubular case 1, that is, the bore 47 includes an allowance space for the eccentric rotating body 23 in a direction along the support rod 41 pivotably supporting the pivotal body 4. Accordingly, the rotation of the rotating body 23 pivotally moves the pivotal body 4 about the support rods 41 within a plane orthogonal to the support rods 41.

Figure 7:
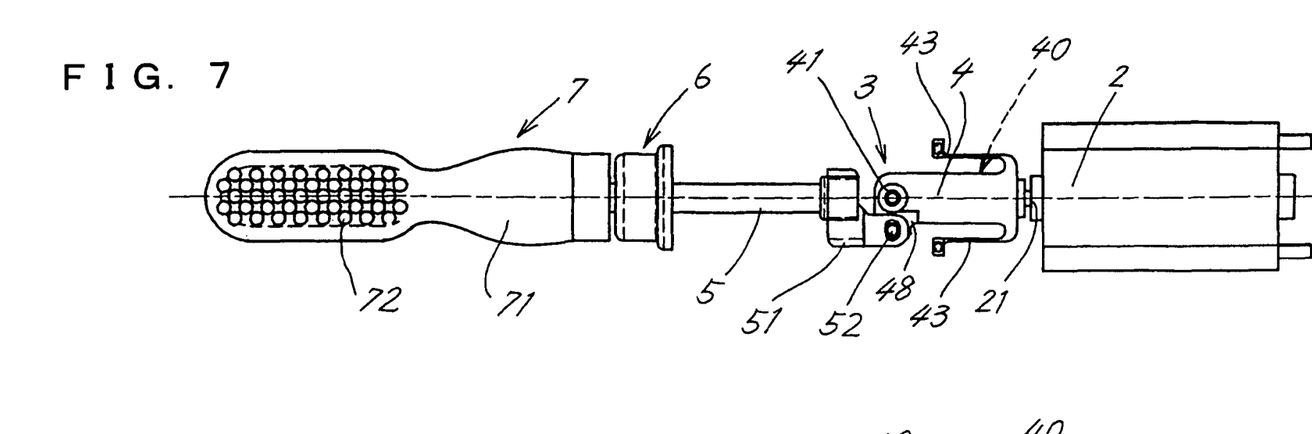
FIG. 7 is a diagram for illustrating motion conversion means.
Figure 10:
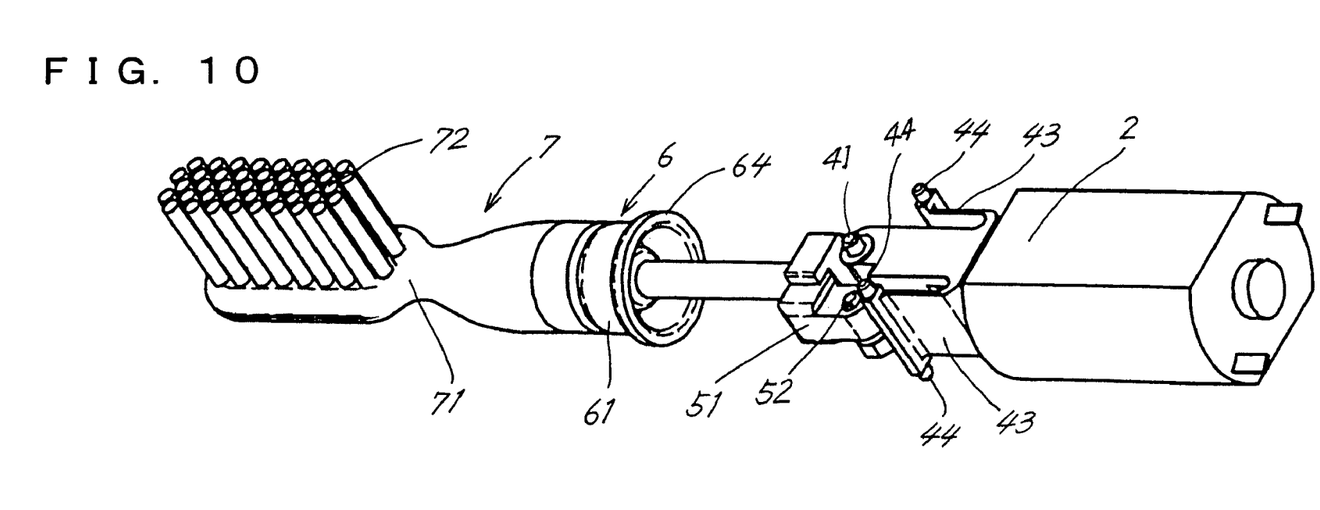
FIG. 10 is a perspective view of the motion conversion means.
Figure 11:
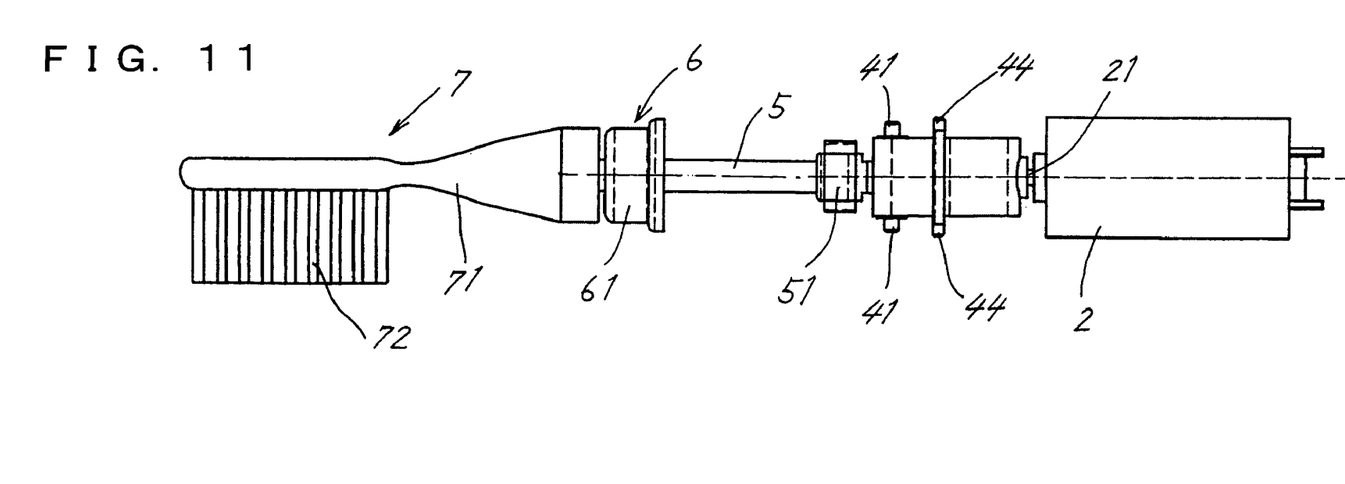
FIG. 11 is a plan view of FIG. 7.

The frame 42 of the pivotal body 4 has flexible support arms 43 projecting therefrom and positioned at opposite ends thereof in the directions of pivotal movement thereof.

Each of the support arms 43 extends a short distance toward the direction of pivotal movement and then extends toward the brush member 7 approximately in parallel to the side face of the pivotal body 4.

The outer end of the support arm 43 has two short pivots 44, 44 extending respectively toward the front and rear sides of the tubular case 1 in parallel to the support shaft 41 and fitted in bearing cavities (not shown) formed respectively in the closure case member 12 and the main case member 11 for the tubular case 1 to support the support arm 43.

The support arms 43 of the present embodiment are each in the form of a thin plate formed from a synthetic resin integrally with the pivotal body 4 and having a widthwise direction orthogonal to the direction of pivotal movement of the pivotal body 4. The support arm 43 readily elastically deforms within the plane of pivotal movement of the body 4 but is difficult to elastically deform in a direction orthogonal to the direction of pivotal movement of the body 4.

In the vicinity of the support rod 41, the pivotal body 4 has a projecting piece 48 projecting in a direction away from the axis of the tubular case 1 in the plane of pivotal movement of the pivotal body 4. The projecting piece 48 is linked to the reciprocating shaft 5 by the connecting member 51.

The connecting member 51 is generally L-shaped and has one end secured to the base end of the reciprocating shaft 5 and the other end provided with a slit 50. A pivot 52 on the projecting piece 48 is engaged in the slit 50.

The slit 50 is elongated in the direction of movement of the pivotal body 4.

A bearing 6 for supporting the reciprocating shaft 5 thereon is liquid-tightly fitted in a forward-end opening of the tubular case 1. The bearing 6 of the present embodiment is a flexible bearing and comprises a cup-shaped body 61 made from a rubber or like flexible material, and an annular portion 63 having an increased thickness and formed by inwardly bending the center of the bottom wall 62 of the body 61 into a tubular form. The reciprocating shaft 5 has an intermediate recessed grooved portion 53, around which the annular portion 63 of the bearing 6 is fitted. With the reciprocating movement of the shaft 5, the bottom wall of the bearing 6 deforms and moves.

A flange 64 is formed along the opening brim of the cup-shaped body 61, which is liquid-tightly fitted in the forward-end opening of the tubular case 1, with the flange 64 fitted in a circumferential groove (not shown) formed in the inner surface of the tubular case 1.

A positioning frame 15 is provided inside the tubular case 1 between the bearing 6 and the motor 2.

The brush member 7 attached to the forward end of the reciprocating shaft 5 comprises a brush head 71 removably fitting around the reciprocating shaft 5, and bristles 72 implanted in the head 71.

With the electric toothbrush described above, one turn of rotation of the motor shaft 21 causes the scotch yoke mechanism 40 to reciprocatingly pivotally move the pivotal body 4 about the support rods 41 with one stroke, and one stroke of reciprocating pivotal movement of the pivotal body 4 causes the brush member 7 to reciprocatingly move along the axis of the tubular case 1 one stroke through the connecting member 51 and the reciprocating shaft 5. Thus, one turn of rotation of the motor shaft 21 causes the brush member 7 on the shaft 5 to perform one forward and backward stroke.

Unlike the conventional electric toothbrush, it is unlikely that the frequency of reciprocating motion of the brush member 7 will become smaller than the number of revolutions of the motor shaft 21.

Since the motor shaft 21, the center of pivotal movement of the pivotal body 4 and the reciprocating shaft 5 are in alignment or agreement with the axis of the tubular case 1, the case 1 can be made smaller in diameter. This means that the tubular case 1 can be designed generally free of limitations and can be so designed that the case 1 is easy to grip. The toothbrush is further free of the problem, such as noise, which is attributable to the backlash to be involved in the meshing engagement of gears since the mechanism used has no meshing gears.

The pivotal body 4 is supported pivotally movably at three points, i.e., by the support rods 41, and two support arms 43. This stabilizes the pivotal movement of the pivotal body 4, enabling the brush member 7 to reciprocatingly move with good stability.

The pivotal body 4 and the support arms 43, 43 are made from a synthetic resin integrally, so that this construction results in no increase in the number of components, obviates the need to attach the support arms 43 to the pivotal body 4 manually and therefore suppresses a rise in cost.

Each of the support arms 43 is in the form of a thin plate made from a synthetic resin integrally with the pivotal body 4 and has a widthwise direction orthogonal to the direction of pivotal movement of the pivotal body 4, so that the support arm 43 is readily elastically deformable within the plane of pivotal movement of the pivotal body but is difficult to elastically deform in a direction orthogonal to the direction of pivotal movement of the pivotal body 4. The pivotal body 4 is therefore movable smoothly with good stability within a plane orthogonal to the support rods 41. This enables the brush member 7 to linearly reciprocatingly move smoothly and stably.

Since the reciprocating shaft 5 slidably extends through and is supported by the flexible bearing 6 provided in the forward-end opening 14 of the tubular case 1, the reciprocating shaft 5 is allowed to reciprocatingly move axially thereof and also to somewhat deflect from the center of the bearing 6. Accordingly, the shaft 5 can be slidably supported free of trouble while being allowed to deflect, even if the pivot 52 on the pivotal body 4 is not smoothly movable through the slit 50 in the connecting member 51 to subject the shaft 5 to some deflective force.

Furthermore, the bearing 6 itself serves also as a seal for preventing the ingress of water through the forward-end opening 14 of the tubular case 1. This decreases the number of components and results in a cost reduction.

FIGS. 12 to 15 show another embodiment of motion conversion means 3 for converting the rotation of the motor shaft 21 into reciprocating motion of the reciprocating shaft 5.

A pivotal body 4 is provided between the motor shaft 21 and the reciprocating shaft 5. The pivotal body 4 is generally U-shaped and comprises a connecting portion 46 extending along the axis of the tubular case 1, a frame 42 projecting from the end of the connecting portion 46 which end is closer to the motor shaft 21 and a bracket 45 projecting from the other end of the portion 46 closer to the reciprocating shaft 5, the frame 42 and the bracket 45 being opposed to each other.

An eccentric rotating body 23 mounted on the forward end of the motor shaft 21 is slidably fitted in the frame 42 to provide a scotch yoke mechanism 40.

A support rod 41 for pivotally movably supporting the pivotal body 4 is positioned at the bent portion of the U-shaped pivotal body 4 which portion is closer to the shaft 5.

The reciprocating rod 5 is supported at its base end by a pivot 52 on the bracket 45.

The reciprocating shaft 5 is slidably supported by a spherical bearing 6a disposed toward the forward end of the tubular case 1 and pivotally movable about the bearing 6a.

With the electric toothbrush according to the second embodiment, one turn of rotation of the motor shaft 21 causes the scotch yoke mechanism 41 to reciprocatingly pivotally move the pivotal body 4 about the support rod 41 by one stroke, and one stroke movement of the body 4 also causes the reciprocating shaft 5 to perform one stroke of forward and backward movement. Thus, one turn of rotation of the motor shaft 21 causes the brush member 7 on the shaft 5 to perform one stroke of reciprocating movement. The reciprocating shaft 5 slidingly moves while slightly deflecting from the center of the spherical bearing 6a.

As in the case of the toothbrush of the first embodiment, it is unlikely that the frequency of reciprocating motion of the brush member 7 will become smaller than the number of revolutions of the motor shaft 21.

Figure 12:
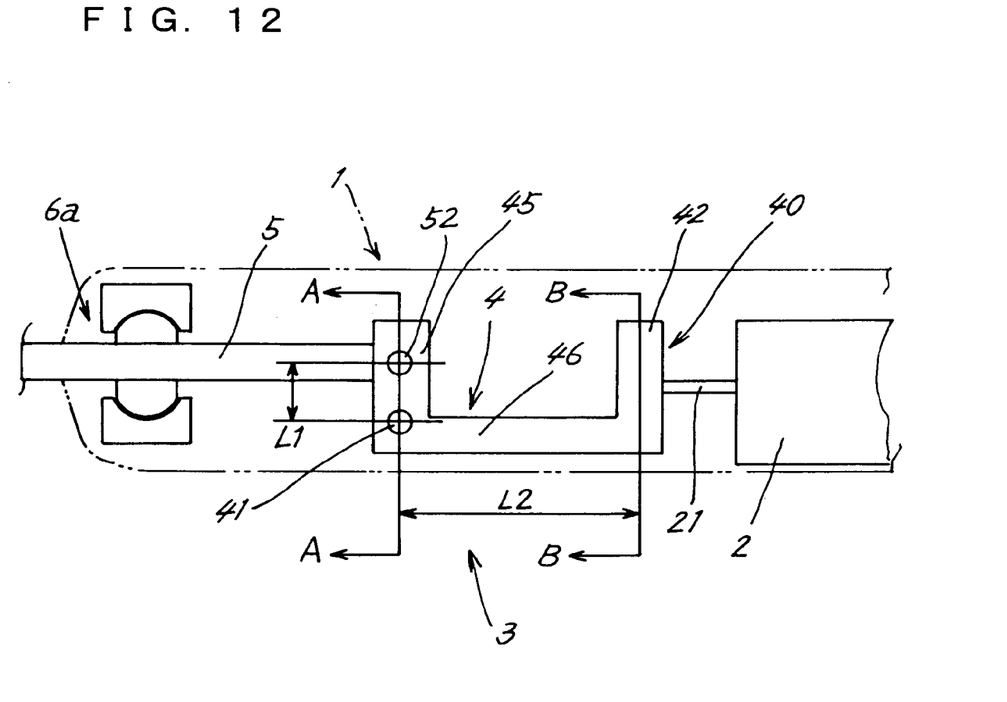
FIG. 12 is a diagram of motion conversion means of a second embodiment.
Figure 13:
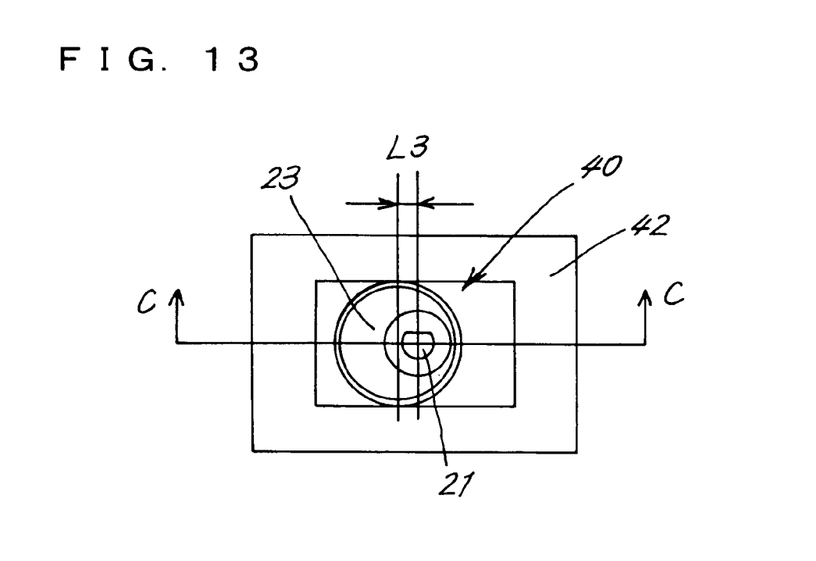
FIG. 13 is a view in section taken along the line B-B in FIG. 12.
Figure 14:
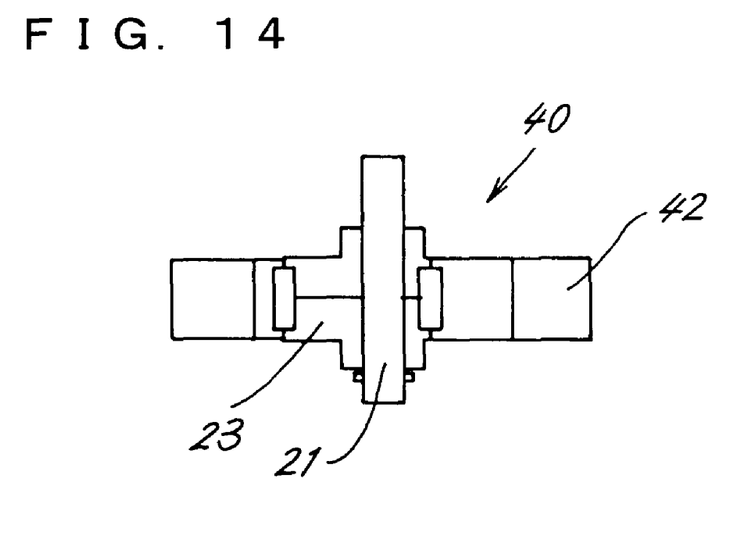
FIG. 14 is a view in section taken along the line C-C in FIG. 13.
Figure 15:
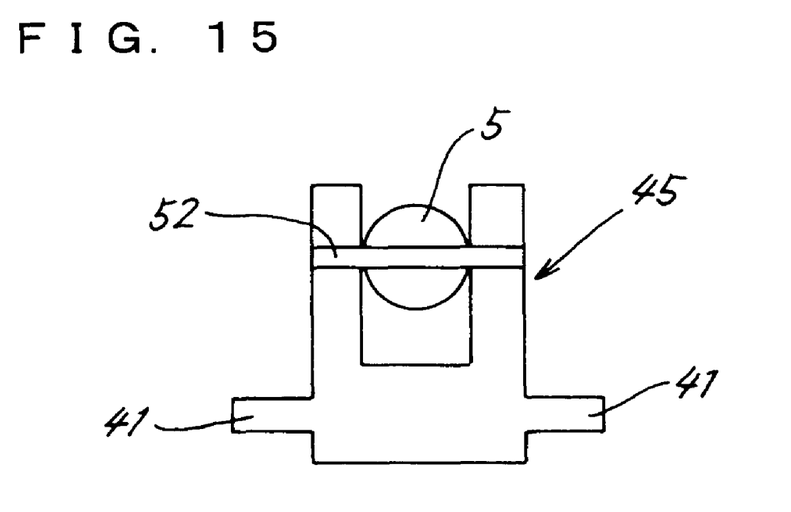
FIG. 15 is a view in section taken along the line A-A in FIG. 12.

According to the present embodiment, the distance L1 between the support rod 41 of the pivotal body 4 and the pivot 51 for the reciprocating shaft 5 is 3.5 mm, the distance L2 from the support rod 41 to the scotch yoke mechanism 40 is 7 mm, the eccentricity L3 of the eccentric rotating body 23 is 0.7 mm, and the stroke of reciprocating motion of the brush member 7 is 0.7 mm.

When the flexible bearing 6 of the first embodiment is used as the bearing fro the reciprocating shaft 5 of the second embodiment, no problem will arise since the flexible bearing 6 permits the deflection of the shaft 5.

Apparently, the present invention can be altered or modified by one skilled in the art without departing from the spirit of the invention. Such modification is included within the scope of the invention as set forth in the appended claims.

What is claimed is:

1. An electric toothbrush comprising a motor housed in a case, motion conversion means for converting the rotation of a motor shaft of the motor into reciprocating motion approximately along an axis of the motor shaft, and a brush member movable with the reciprocating motion, the motor shaft being provided with an eccentric rotating body rotatable with the rotation of the motor shaft, the motion conversion means having a pivotal body supported by a rod and pivotally movable in a plane orthogonal to the motor shaft, the pivotal body having a rectangular frame for the eccentric rotating body to slidably rotatably fit in and being pivotally movable by the rotation of the eccentric rotating body, the motion conversion means further having a reciprocating shaft provided with the brush member and connected to another portion of the pivotal body to reciprocatingly move with the pivotal movement of the pivotal body and to cause the brush member to perform reciprocating motion, wherein the pivotal body is pivotally movably supported by the support rod, and the reciprocating shaft is connected by a connecting member to a pivot positioned in the vicinity of the support rod and away from the axis of the case toward a direction orthogonal to the axis of the case.

2. An electric toothbrush comprising a tubular case serving also as a handle, a motor housed in the tubular case so as to position a motor shaft approximately along an axis of the tubular case, a reciprocating shaft coupled to the motor shaft by motion conversion means for converting the rotation of the motor shaft into reciprocating motion approximately along the axis of the tubular case, and a brush member attached to the reciprocating shaft, the motion conversion means having a pivotal body pivotally movable about a support rod extending in a direction orthogonal to the motor shaft, and an eccentric rotating body provided on the motor shaft and engaged with of the pivotal body positioned toward the motor shaft for pivotally moving the pivotal body so as to provide a scotch yoke mechanism, the reciprocating shaft being pivotally connected to the pivotal body to cause the brush member to perform reciprocating motion, wherein the pivotal body is pivotally movably supported by the support rod, and the reciprocating shaft is connected by a connecting member to a pivot positioned in the vicinity of the support rod and away from the axis of the tubular case toward a direction orthogonal to the axis of the tubular case.

3. The electric toothbrush according to claim 2 wherein the pivotal body has a flexible support arm extending toward the brush member from each of opposite ends thereof in the directions of pivotal movement thereof, and the support arm has an outer end held by the tubular case.

4. The electric toothbrush according to claim 3 wherein the support arm is in the form of a thin plate made from a synthetic resin integrally with the pivotal body and having a widthwise direction orthogonal to the direction of pivotal movement of the pivotal body, the support arm being readily elastically deformable within the plane of pivotal movement of the pivotal body and difficult to elastically deform in a direction orthogonal to the direction of pivotal movement of the pivotal body.

5. The electric toothbrush according to claim 2 wherein the reciprocating shaft extends through and is supported by a flexible bearing disposed at a forward end of the tubular case.

6. The electric toothbrush according to claim 2 wherein the pivotal body is generally U-shaped and comprises a connecting portion, and a rectangular frame and a bracket which are joined respectively to opposite ends of the connecting portion and opposed to each other, the eccentric rotating body being slidably rotatably fitted in the frame, the reciprocating shaft being pivotally connected to the pivotal body by a pivot supported on the bracket, the support rod being positioned in the vicinity of a bent portion of the pivotal body on the pivot side thereof and positioned in parallel to the pivot, the reciprocating shaft being pivotally movably supported by a bearing at a forward end of the tubular case.

* * * * *